United States Patent [19]

Frye et al.

[11] Patent Number: 5,076,094
[45] Date of Patent: Dec. 31, 1991

[54] DUAL OUTPUT ACOUSTIC WAVE SENSOR FOR MOLECULAR IDENTIFICATION

[75] Inventors: Gregory C. Frye, Cedar Crest; Stephen J. Martin, Albuquerque, both of N. Mex.

[73] Assignee: The United States of America as represented by the United States Department of Energy, Washington, D.C.

[21] Appl. No.: 592,383

[22] Filed: Oct. 3, 1990

[51] Int. Cl.$^5$ .................. G01N 29/18; G01N 29/20; G01N 29/24

[52] U.S. Cl. ............................ 73/19.03; 73/24.01; 73/24.03; 73/24.04; 73/24.06; 73/61.1 R; 73/590; 73/597; 73/599; 310/313 R; 310/313 B

[58] Field of Search .............. 73/19.03, 24.01, 24.03, 73/24.06, 24.04, 61 R, 61.1 R, 590, 597, 599, 602, 643; 310/313 R, 313 D, 313 B

[56] References Cited

U.S. PATENT DOCUMENTS

| | | | |
|---|---|---|---|
| 4,055,072 | 10/1977 | Fletcher et al. | 73/24.01 |
| 4,312,228 | 1/1982 | Wohltjen | 73/597 |
| 4,361,026 | 11/1982 | Muller et al. | 73/24.01 |
| 4,759,210 | 7/1988 | Wohltjen | 73/23 |
| 4,818,348 | 4/1989 | Stetter | 73/23.2 |
| 4,895,017 | 1/1990 | Pyke et al. | 73/23 |
| 4,947,677 | 8/1990 | Frye et al. | 73/38 |

OTHER PUBLICATIONS

H. Wohltjen, "Mechanism of Operation and Design Considerations for Surface Acoustic Wave Device Vapour Sensors", Sensors and Actuators, vol. 5, 1984, pp. 307-325.

W. Carey et al., "Selection of Adsorbates for Chemical Sensor Arrays by Pattern Recognition", Analytical Chemistry, vol. 58, No. 1, Jan. 1986, pp. 149-153.

S. Rose-Pehrsson et al., "Detection of Hazardous Vapors Including Mixtures Using Pattern Recognition Analysis of Responses from Surface Acoustic Wave Devices", Analytical Chemistry, vol. 60, No. 24, Dec. 15, 1988.

M. Nieuwenhuizen et al., "Surface Acoustic Wave Chemical Sensors", Sensors and Materials, vol. 5, 1989, pp. 261-300.

S. Martin et al., "Effective Utilization of Acoustic Wave Sensor Responses: Simultaneous Measurement of Velocity and Attenuation", IEEE 1989 Ultrasonics Symposium, Oct. 3-6, 1989, Montreal, Quebec, Canada, pp. 621-625.

Primary Examiner—Hezron E. Williams
Assistant Examiner—Rose M. Finley
Attorney, Agent, or Firm—Karla Ojanen; James H. Chafin; William R. Moser

[57] ABSTRACT

A method of identification and quantification of absorbed chemical species by measuring changes in both the velocity and the attenuation of an acoustic wave traveling through a thin film into which the chemical species is sorbed. The dual output response provides two independent sensor responses from a single sensing device thereby providing twice as much information as a single output sensor. This dual output technique and analysis allows a single sensor to provide both the concentration and the identity of a chemical species or permits the number of sensors required for mixtures to be reduced by a factor of two.

48 Claims, 8 Drawing Sheets

DUAL OUTPUT ACOUSTIC WAVE SENSOR FOR MOLECULAR IDENTIFICATION

The United States Government has rights in this invention pursuant to Contract No. DE-AC04-76DP00789 between the Department of Energy and American Telephone & Telegraph Company.

BACKGROUND OF THE INVENTION

This invention relates generally to the real-time detection of chemical species, and more particularly, relates to a method and apparatus for the detection, identification and quantification of chemical species using acoustic waves.

Real-time detection of chemical species is necessary to protect the environment, to minimize worker exposure to toxic chemicals and to efficiently control industrial processes. The detection, identification and quantification of dilute concentrations of chemical species in ambient environments or industrial processes generally require sophisticated analytical equipment such as gas chromatography and mass spectrometry. The cost and bulkiness of these devices and the long times required to perform a chemical analysis make these devices inappropriate for real-time detection of chemical species.

Chemical sensors provide an inexpensive, sensitive and small apparatus for detecting chemical species One type of chemical sensor is based on the use of acoustic wave (AW) devices, particularly surface acoustic wave (SAW) devices, but also including acoustic plate mode (APM) devices and Lamb wave devices, use two interdigitated electrodes on a piezoelectric substrate such as quartz to launch and detect an acoustic wave which can interact with the environment or a coating applied to the device substrate while travelling between the two electrodes. As an example, a method and apparatus for using a SAW device to detect a chemical species in a fluid is disclosed in U.S. Pat. No. 4,312,228, entitled "Methods of Detection with Surface Acoustic Wave and Apparati Therefor" to Wohltjen and is further described in H. Wohltjen, published in SENSORS AND ACTUATORS, Vol. 5, pp. 307-325 (1984). Wohltjen teaches that chemical species can be detected with SAW devices, the surfaces of which are coated with materials which selectively interact with a different chemical species. The interaction between the chemical species and the surface coating is detected by monitoring changes in the frequency, the phase or the attenuation of the surface acoustic wave. The magnitude of the change of one of these properties of the surface acoustic wave indicates the concentration of the species interacting with the surface material.

M. S. Nieuwenhuizen and A. Venema in an article entitled "Surface Acoustic Wave Chemical Sensors", SENSORS AND MATERIALS, Vol. 1, pp. 261-300 (1989) further describe selective coatings for SAW devices and how these selective coatings are used to prepare coated SAW devices to detect a particular chemical species. But there are only a few examples where a coating material preferentially interacts with one species to the exclusion of others. Moreover, these coating materials often irreversibly bind the chemical species of interest because of the strong chemical interactions required to achieve this level of selectivity; thereby reducing sensor lifetime and decreasing the maximum detectable concentration. Because these coatings only detect one species, another shortcoming of this type of coated SAW device is that for each chemical species to be detected, a separate coated SAW device is required, which for some practical applications where it is desirable to detect a large number of chemical species, an unreasonably large number of coated SAW devices is necessary.

To overcome these shortcomings, an alternative approach is the use of an array of SAW devices with coating materials which, while sorbing a variety of chemical species, exhibit some selectivity in the amount of sorption. Thus, the relative magnitudes of the responses of different coated SAW devices will depend on the chemical species providing the responses. Using pattern recognition techniques, the responses from such an array of coated SAW devices can be analyzed to determine the presence and concentration of the chemical species providing the responses. Such use of pattern recognition schemes for data analysis from an array of chemical sensors has been described by Carey et al., ANALYTICAL CHEMISTRY, Vol. 58, pp. 149-153 (1986) and Rose-Pehrsson et al. in ANALYTICAL CHEMISTRY, Vol. 60, pp. 2801-2811 (1988).

Practical application of chemical sensors arrays and pattern recognition schemes has been hindered by the need for multiple sensors, by variability in preparation of the coating materials and the difficulty of obtaining discriminating coating materials for certain chemical species. Typically, four to twelve different coated sensors in an array are used and the complexity and expense increase with the number of sensors. The variability in the coating materials from one sensor array to another requires elaborate calibration of each sensor array corresponding to the chemical species of interest for accurate detection and quantification. Finally, because the magnitude of responses to various chemicals is dependent upon the chemical interactions between the species and the coating materials, and because many chemical species have similar chemical properties to other chemical species which may be present, it is difficult to prepare a set of coating materials which can discriminate between similar species.

Another technique for identifying chemical species which provides a SAW device response is disclosed in U.S. Pat. No. 4,895,017, entitled "Apparatus and Method for Early Detection and Identification of Dilute Chemical Vapors" to Pyke et al. In this technique, the transient responses of one or more coated SAW devices are monitored to determine the time constants for sorption into the coating materials. Time constants vary significantly for different chemical species, therefore the time constants empirically identify the species providing the responses and the magnitudes of the responses determine the concentration of the sorbing species. This technique has the disadvantage of requiring a sophisticated analytical procedure such as, for example, a Kalman filter technique to efficiently analyze the transient response and determine the time constant. Note that the time constant for sorption is significantly larger than the sampling period for the SAW sensor responses, therefore an apparatus which permits rapid sampling is required. But coating materials which provide rapid sorption properties are ineffective with this technique because the time constant for sorption is too small to be quantitatively identified. The discriminating ability increases if the time constant for sorption of different chemical species varies dramatically. However, this limits the speed of the sensor since an analysis of the transients for the long time constant species will require monitoring the responses for long times and, in order to remove the sorbed species after detection to regenerate the sensor, even longer times will be required to fully desorb the chemical species from the coating material. An additional complication is the fact that the time constant for sorption can depend on the concentration of the sorbing species as well as the presence or absence of other chemical species.

SUMMARY OF THE INVENTION

The invention comprises a method for the identification and quantification of sorbed chemical species onto a coating of a device capable of generating and receiving an acoustic wave, by measuring the changes in the velocity of the acoustic wave resulting from the sorption of the chemical species into the coating as the wave travels through the coating and by measuring the changes in the attenuation of an acoustic wave resulting from the sorption of the chemical species into the coating as the wave travels through the coating. The inventive method further correlates the magnitudes of the changes of velocity with respect to changes of the attenuation of the acoustic wave to identify the sorbed chemical species. The absolute magnitudes of the velocity changes or the absolute magnitude of the attenuation changes are used to determine the concentration of the identified chemical species.

An apparatus for detecting and identifying at least one unknown chemical species has also been invented which comprises at least one acoustic wave device coated with a material, said material having properties which change upon sorption of a chemical species, means for measuring the velocity of an acoustic wave traveling through said material, means for measuring the attenuation of the acoustic wave traveling through said material, sampling means to contact said acoustic wave device to an unknown chemical species for sorption into the coating material, means for determining the changes in both the attenuation and velocity values of the acoustic wave upon sorption of the unknown chemical species, and means for comparing the values of the velocity and attenuation changes to known values of known chemical species in order to identify and quantify the unknown sorbed chemical species.

Accordingly, it is an object of the present invention to use a single acoustic wave device, especially a SAW device, to rapidly detect the presence of a chemical substance, to determine the molecular identity of that chemical species and to evaluate the concentration of this species in either a gas or liquid environment. It is a further object of this invention to minimize the number of acoustic wave devices in an array that will be able to detect the presence of multiple chemical substances, determine their molecular identities and evaluate their concentrations in either a gas or liquid environment. The dual output technique provides two independent sensor responses from a single sensing device and allows both the concentration and the identity of a single molecular species to be determined with a single sensor thereby providing twice as much information as a single output sensor. This method advances the art of chemical species detection because one single device now replaces two single output sensors that would be required to obtain as much information. In other words, where N single output sensors normally would be required to determine the concentrations of N species, the technique described herein permits the use of only N/2 sensors. This advantage allows the production of cheaper and less complex sensing systems. These and other objects and advantages of the present invention will be apparent from the attached figures and the description of the preferred embodiment of the invention that follow.

DESCRIPTION OF THE PREFERRED EMBODIMENT

The technique to determine both concentration and molecular identification of a gaseous or liquid phase species based on the response of a single acoustic wave (AW) device uses the simultaneous measurement of both the velocity and the attenuation, i.e., the rate of decay, of the wave as the wave travels along the substrate and interacts with a thin film formed on the device surface. When the film sorbs a chemical species of interest, the mass density of the film increases with a corresponding decrease in the wave velocity. Because of this interaction, there is no significant change in the wave attenuation. The magnitude of the effect of the sorption on the wave velocity depends on the number of molecules sorbed and the molecular weight of the sorbing species.

When sorption alters other properties of the film such as the viscoelastic properties of a polymer film, the interaction of the wave with the film alters both the velocity and the attenuation of the wave. This additional response affecting the attenuation is dependent upon the nature of the coating and the interaction of the sorbing species with the coating.

Note that the response of wave velocity to a sorbed chemical species depends on the sorbed mass, but the attenuation response is independent of mass and is dependent upon the alteration in the film properties. Hence the attenuation and the velocity response are independent responses. In the simplest case, the velocity shift alone can be used to determine the concentration of the sorbing species while the ratio of the attenuation shift to the velocity shift can be used to determine the specific chemical species being sorbed by the film. Thus, a single AW device can be used to simultaneously identify the molecular species and determine the concentration of that species in either the gas or liquid phase in contact with the device. The invention described herein can be used to identify and quantify chemical compounds of known chemical composition. The technique and apparatus herein is also useful to identify and quantify chemical species or compounds which have been transferred from a liquid or solid sample to the gas or liquid phase in contact with the device.

Typically, acoustic wave devices are an arrangement of input and output interdigital transducers formed on a piezoelectric substrate such as quartz or lithium niobate. The input transducer, upon application of an alternating voltage, generates an alternating mechanical strain field because of the piezoelectric nature of the substrate. The alternating mechanical strain field launches an acoustic wave which if the wave travels along the substrate surface is called a surface acoustic wave (SAW) and if the wave travels through the bulk of the substrate is called an acoustic plate mode (APM). The acoustic wave interacts with a thin film formed on the device surface and then is reconverted into an electrical signal by the output transducer.

The acoustic wave device may have variations in its structure. For example, the interdigitated transducers may be lithographically patterned from a metallized layer, such as aluminum or a gold-on-chrome composite, onto the substrate. And, the substrate between the input and output interdigital transducer does not necessarily have to be piezoelectric, but may be coated with any piezoelectric coating material, two examples of which are zinc oxide or aluminum nitride.

Figure 1A:
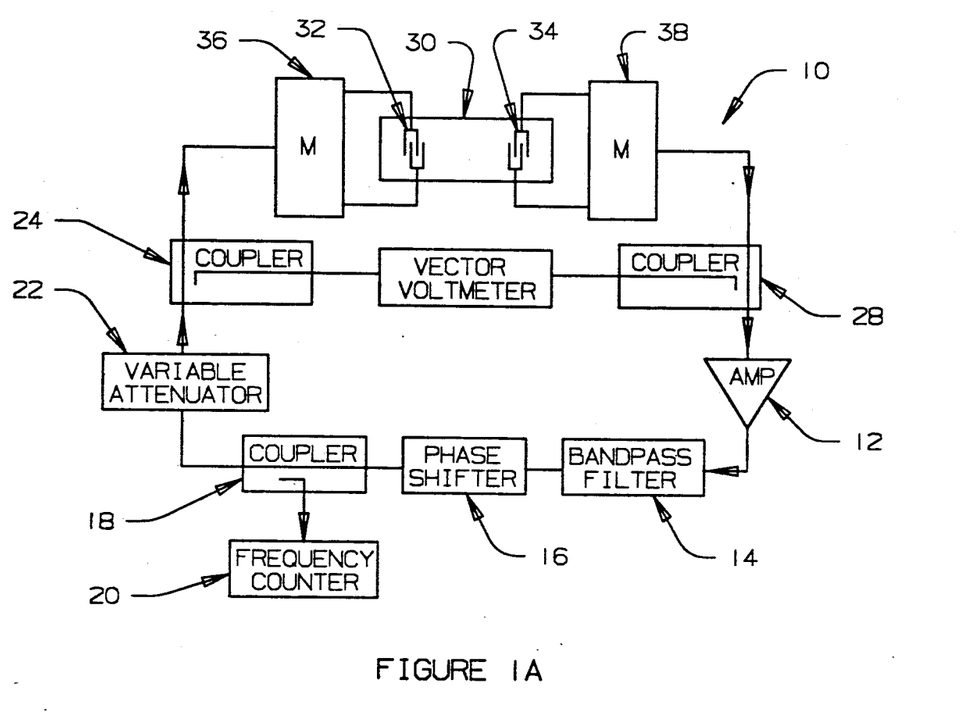
FIGS. 1A and 1B are schematics of a electronic system for operating acoustic wave devices with the dual output technique of the invention.

The velocity of the wave can easily be determined by operating the device as the feedback element of a oscillator circuit using an RF amplifier as shown in FIG. 1A. In this configuration, relative changes in frequency (f) can be directly related to relative changes in wave velocity (v). In situations where the velocity shift ($\Delta v$) is dominated by changes in the mass density of the film (m, mass/area), these frequency changes ($\Delta f$) can be directly related to changes in mass density by:

$$\frac{\Delta f}{f_o} = \frac{\Delta v}{v_o} = -c_m f_o m,$$

where $c_m$ is a mass sensitivity constant which depends on the piezoelectric substrate, and the subscript "o" indicates the unperturbed velocity or frequency.

Figure 1B:
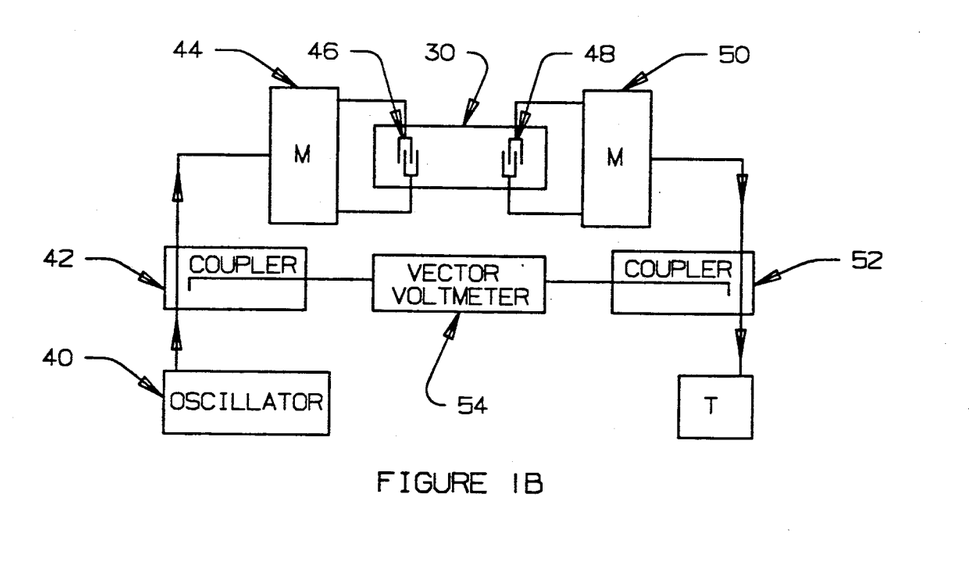

FIGS. 1A and 1B illustrate the dual output measurement system 10 of the invention and more specifically illustrate two techniques to obtain the velocity/attenuation measurements. FIG. 1A illustrates an oscillator technique which, at minimum utilizes the RF amplifier 12 to operate the acoustic wave device 30. The wave velocity is measured by operating the acoustic wave device 30 as the feedback element of an oscillator loop using the RF amplifier 12 to amplify the signal from the output transducer 34. This output signal is sent to the input transducer 32, where the frequency of oscillation is monitored using directional coupler 18 to split off a fraction of the power in the oscillator loop to a frequency counter 20. At this point the velocity shift ($\Delta v$) is determined from the frequency shift ($\Delta f$) using $\Delta f/f_o = K\Delta v/v_o$ where K is the fraction of the acoustic wave path covered by the material which is sorbing the chemical species and $v_o$ and $f_o$ are the unperturbed velocity and frequency, respectively. The attenuation of the power of the wave is measured using directional couplers 28 and 24 to split off a fraction of the power at the input and output transducers 32, 34 to the acoustic wave device 30. Power levels are measured using a vector voltmeter 26, a power meter (not shown) or similar detection means. Bandpass filter 14, phase shifter 16, variable attenuator 22, and matching impedance networks 36 and 38 all operate to refine the signal as it is processed.

FIG. 1B illustrates the generated signal technique which is similar to the measurement system and technique of FIG. 1A, but the system of FIG. 1B utilizes an external signal generator, such as a synthesized signal generator (not shown) or an oscillator 40 to generate an acoustic wave of known frequency. A vector voltmeter 54 is used to determine the difference in phase and power between input transducer 46 and output transducer 48 which signals are obtained from a division of a portion of the signal at couplers 42 and 52, respectively. The differences in phase and power of the signal at these points will be used to determine velocity shift and attenuation shift respectively. Changes in phase of the output signal are monitored using a vector voltmeter 54 or similar detection means and the changes in phase of the acoustic wave are related to changes in wave velocity. Alternatively, the frequency of the signal from the external source is adjusted to maintain a constant phase value and the velocity shift ($\Delta v$) is determined from the frequency shift ($\Delta f$) using $\Delta f/f_o = K\Delta v/v_o$ where x is the fraction of the acoustic wave path covered by the material which is sorbing the chemical species and $v_o$ and $f_o$ are the unperturbed velocity and frequency, respectively. Changes in power of the acoustic wave are related to the attenuation of the wave and are measured as described with respect to FIG. 1A.

Typical AW chemical sensors utilize a thin film coating which sorbs or binds the chemical species to be detected and when the sorption/binding is selective for the chemical species of interest, a selective chemical sensor is obtained. Because this selectivity is far from being perfect, an array of sensors with different coatings are used along with a pattern recognition scheme to determine the concentrations of multiple species in a mixture. Each AW device produces a single response proportional to the mass of sorbed/bound species. Thus, a single sensor can determine the concentration of a single species assuming the species sorbed is known by some independent means. For a mixture containing N species, an array of N sensors can be used to determine the concentrations of the N species if the sensor responses are all independent.

The discriminating capability to identify and quantify the sorbed chemical species with a single acoustic wave device of our inventive dual output technique employs polymer coatings on the substrate of a device which exhibit viscoelastic changes resulting from the sorption of chemical species. These techniques have predominantly used surface acoustic wave devices for detection of gas phase species.

Figure 2:
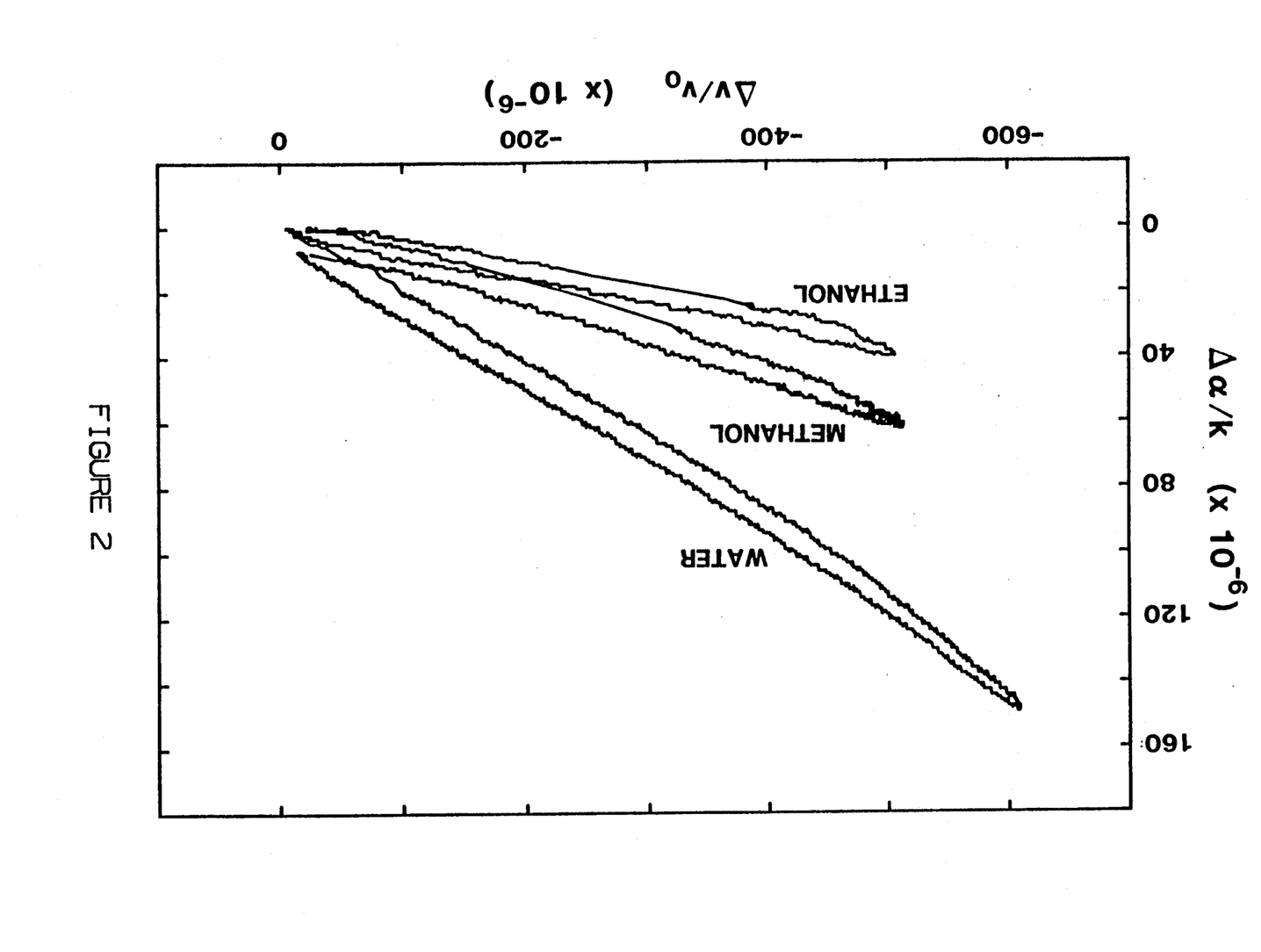
FIG. 2 is a plot of attenuation shift vs. velocity shift for a polyimide-coated SAW device during sorption of water, methanol and ethanol.

If the wave attenuation shift, $\Delta\alpha/k$ where $\alpha$ is attenuation and k, the wavenumber, equals $2\pi/\lambda$ where $\lambda$ is the wavelength, is plotted as a function of the velocity shift, a curve is traced out which is a function of the species being sorbed. In fact, significantly different curves are traced out for the various species. The results for water, methanol, and ethanol as the sorbing species and polyimide as the coating material are shown in FIG. 2. A comparison of these sensor responses resulting from sorption of an unknown species to these calibration curves allows the species being sorbed to be identified.

Figure 3:
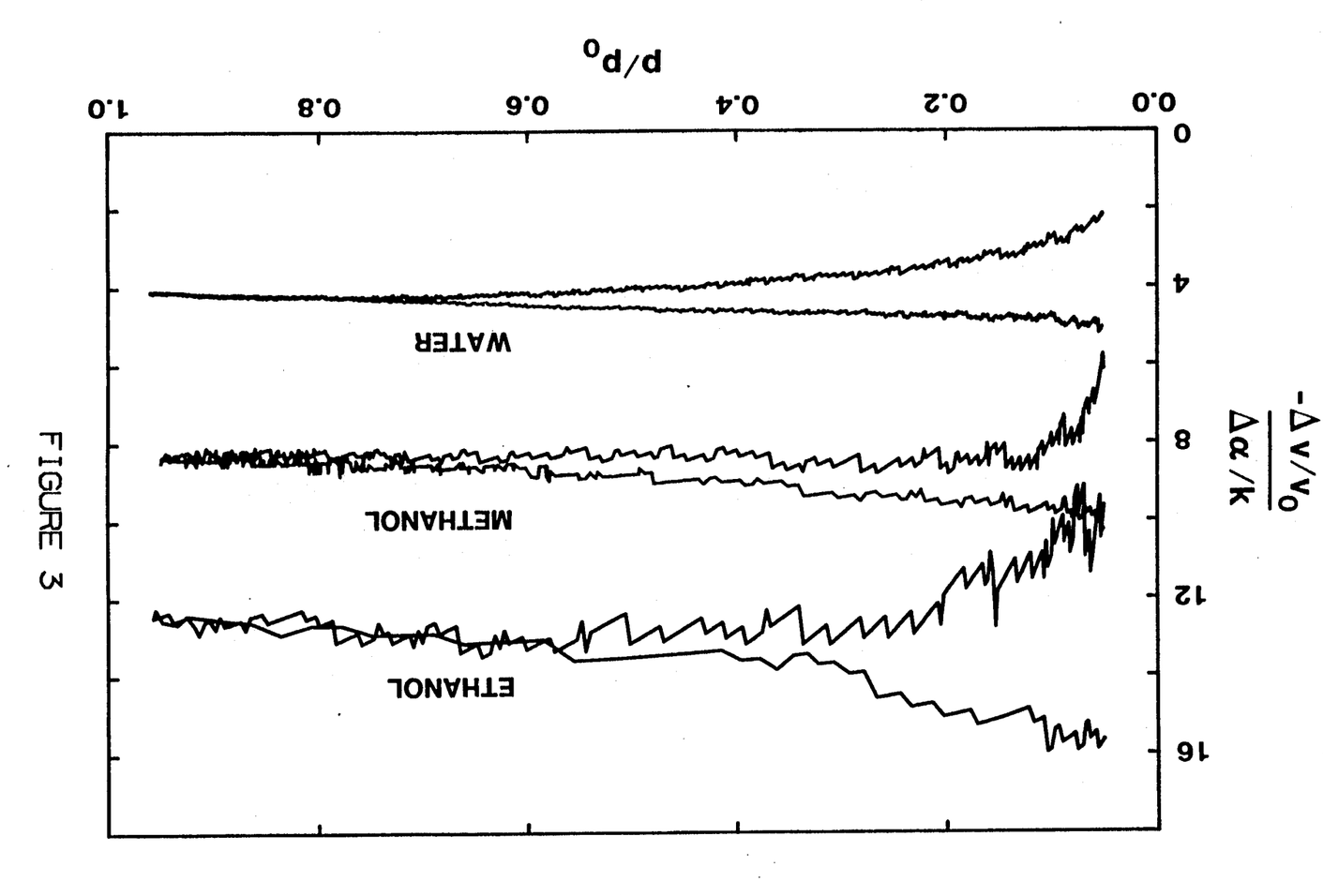
FIG. 3 is a plot of the ratio of velocity shift to attenuation shift versus the gas phase concentration for water, methanol and ethanol sorbing into a polyimide film.

When the ratio of velocity shift to attenuation shift is plotted versus the gas phase concentration, a relatively constant value is obtained for the various species, as shown in FIG. 3. FIG. 3 is a plot of the ratio of velocity shift to attenuation shift versus the gas phase concentration for water, methanol and ethanol sorbing into a polyimide film. In the ratio, $p/p_o$, p represents the partial pressure of the sorbing species and $p_o$ is saturation vapor pressure of the sorbing species at a particular temperature. Since the velocity/attenuation ratio has a fairly constant value for each species, a simple technique for identifying the species providing a given sensor response is to calculate this ratio and compare it to the values for each species.

Although the most discriminating responses are obtained using a polyimide film, the polyimide film has the disadvantage that it is glassy and, therefore, exhibits slow diffusional properties. This slow diffusion, exhibited by the significant hysteresis seen in FIG. 2, makes the evaluation of larger species, for which diffusion rates are even lower, difficult. Thinner films may make the diffusion times shorter but sensitivity of the device may decrease when the thin films are used.

Figure 4:
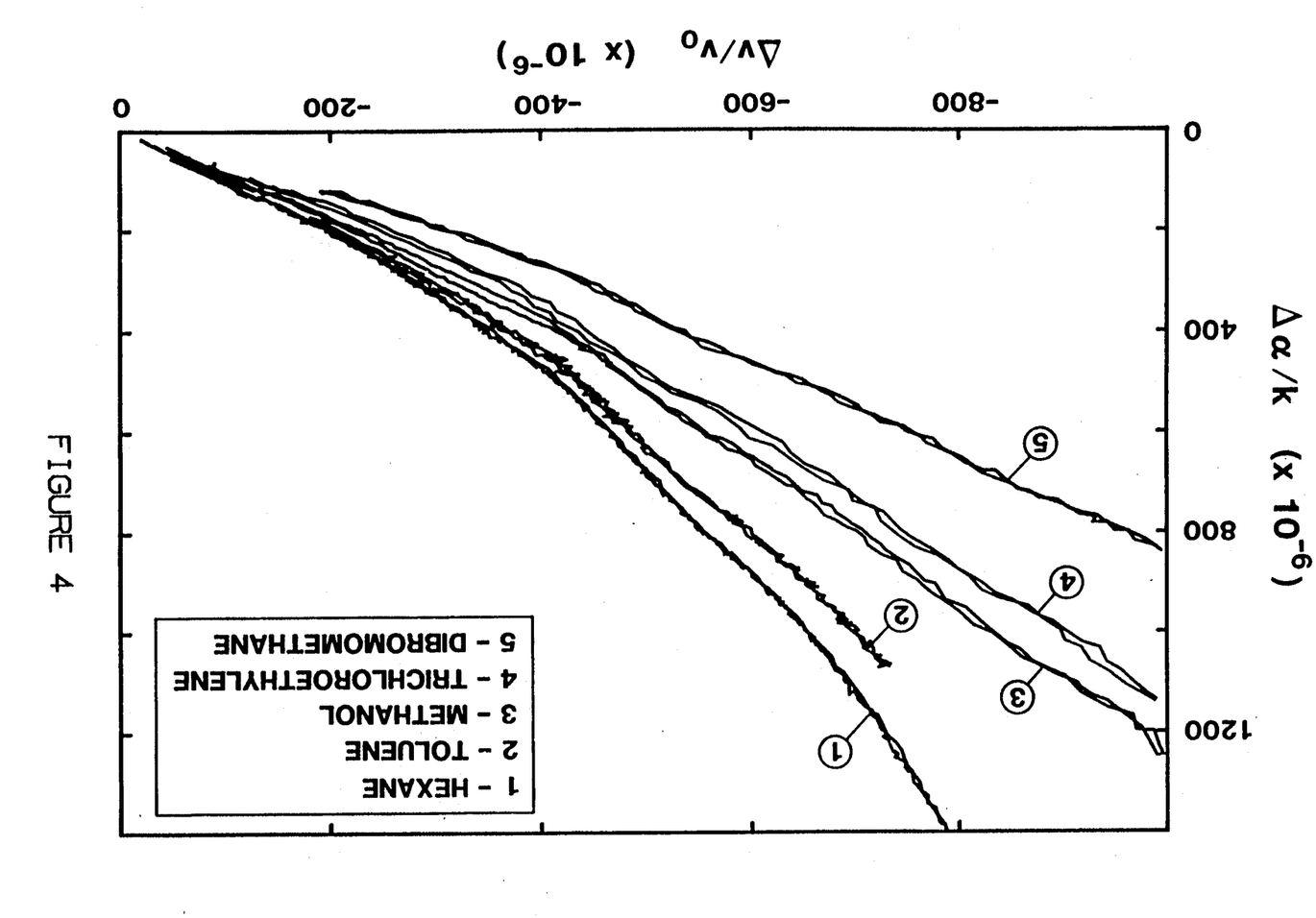
FIG. 4 is a plot of attenuation shift vs. velocity shift for a polysiloxane-coated SAW device during sorption of various species.

Polymers exhibiting rapid diffusional properties such as polysiloxane, polybutadiene and polyisoprene also provide a medium for the acoustic wave. FIG. 4 illustrates molecular discrimination and quantification of five sorbed chemical species using a polysiloxane film. In contrast to the polyimide, the hysteresis in the curves is low, especially for nonpolar species like hexane and toluene. Again, since the curves are distinct, a comparison of the values obtained resulting from sorption of an unknown species to these calibration curves allows the species providing the response to be identified. For example, the proximity of a response of $\Delta v/v_o = -6 \times 10^{-4}$ and $\Delta \alpha/k = 6 \times 10^{-4}$ to the curve for trichloroethylene would be used to identify the species providing this response as trichloroethylene.

Since these curves are fairly simple, a metric for each species can be obtained by determining the velocity shift at a constant value of attenuation shift. These values (at $\Delta \alpha/k = 1.0 \times 10^{-3}$) are reported for a variety of common chemical species in Table I. Even though several species, such as n-dodecane, acetone, toluene and 3-methylpentane, have similar velocity shift values, these species are of similar nature, being relatively low liquid density, nonpolar solvents. In fact, the velocity shift values increase linearly with liquid density for the nonpolar species which have a high affinity for the nonpolar polysiloxane coated film. This particular response enables prediction of expected responses for certain chemical species based on their liquid density values and allows the efficient discrimination between molecular species having different liquid densities.

TABLE I

| Velocity shift when the attenuation shift equals $1.0 \times 10^{-3}$ for a polysiloxane coated SAW device (see FIG. 4). | | |
|---|---|---|
| Molecular Species | Velocity Shift ($\times 10^{-3}$) | Liquid Density (g/cm$^3$) |
| Hexane | 0.610 | 0.6603 |
| 3-Methylpentane | 0.669 | 0.6645 |
|  | 0.630 |  |
| n-Dodecane | 0.684 | 0.7487 |
| Isopropanol | 0.762 | 0.7855 |
|  | 0.790 |  |
|  | 0.830 |  |

TABLE I-continued

| Velocity shift when the attenuation shift equals $1.0 \times 10^{-3}$ for a polysiloxane coated SAW device (see FIG. 4). | | |
|---|---|---|
| Molecular Species | Velocity Shift ($\times 10^{-3}$) | Liquid Density (g/cm$^3$) |
|  | 0.835 |  |
| Ethanol | 0.782 | 0.7893 |
|  | 0.787 |  |
| Acetone | 0.659 | 0.7899 |
| Methanol | 0.763 | 0.7914 |
|  | 0.772 |  |
| Toluene | 0.658 | 0.8669 |
|  | 0.654 |  |
| Trichloroethylene | 0.832 | 1.4642 |
|  | 0.823 |  |
| Dibromomethane | 1.068 | 2.497 |
|  | 1.068 |  |
|  | 1.061 |  |
|  | 1.059 |  |

Figure 5:
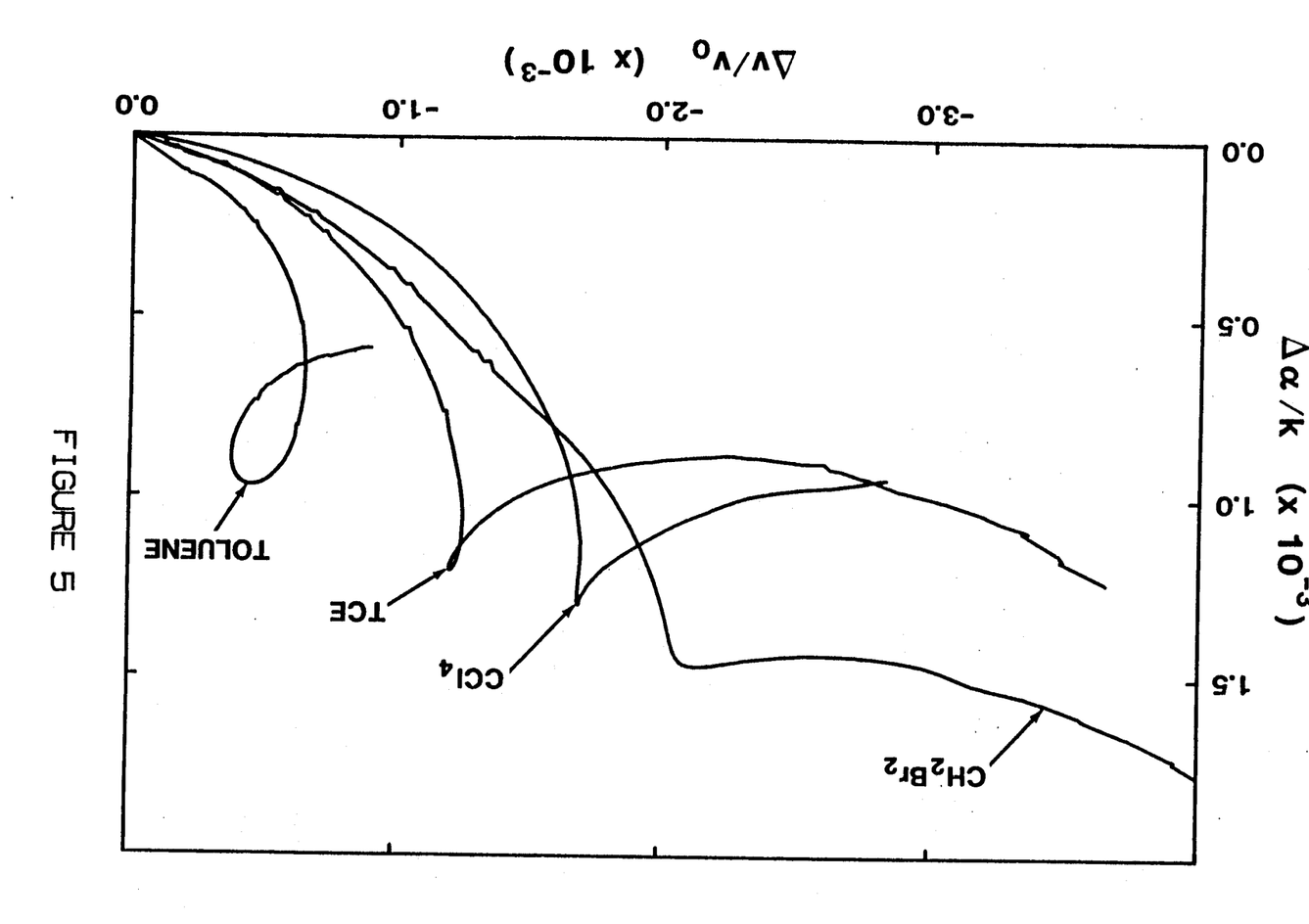
FIG. 5 is a plot of attenuation shift vs. velocity shift for a polybutadiene-coated SAW device during sorption of various species.
Figure 6:
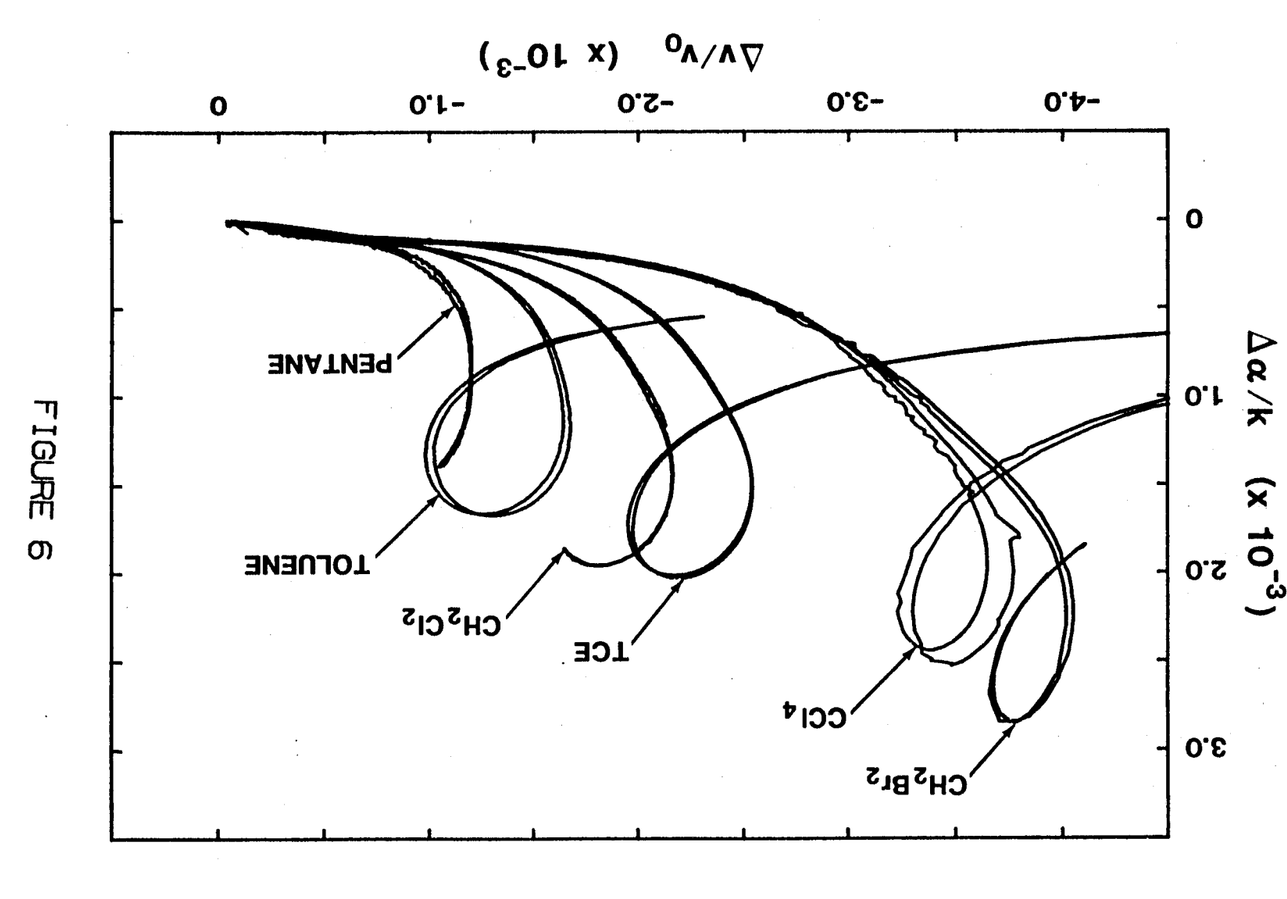
FIG. 6 is a plot of attenuation shift vs. velocity shift for a copolymer-coated SAW device during sorption of various species.

This type of dependency is observed with other nonpolar films such as polybutadiene and polyisoprene films; the film used to obtain the results of FIG. 6 is a copolymer of 80% polybutadiene and 20% polystyrene. Note that, as shown in FIGS. 5 and 6, more complex attenuation curves indicate large changes in the viscoelastic properties of these films. Again, it is seen that different species trace out unique curves making it possible to identify the molecular species. The velocity shift at the point where the attenuation is at a maximum can be used as a metric by plotting this velocity shift at the maximum against the liquid density of the sorbed chemical species. A linear response is obtained.

The dependence of the responses on liquid density makes these films especially useful for discriminating between chlorinated (high liquid densities: 1.4 to 1.6 g/cm$^3$) and nonchlorinated (low liquid densities: 0.6 to 0.9 g/cm$^3$) hydrocarbons. Chlorinated hydrocarbons are volatile durable species of environmental concern and have been implicated in ozone depletion and are known carcinogens. Thus, a simple, single device sensor which identifies the presence of chlorinated species is a significant and important application of this dual output sensor.

Figure 7:
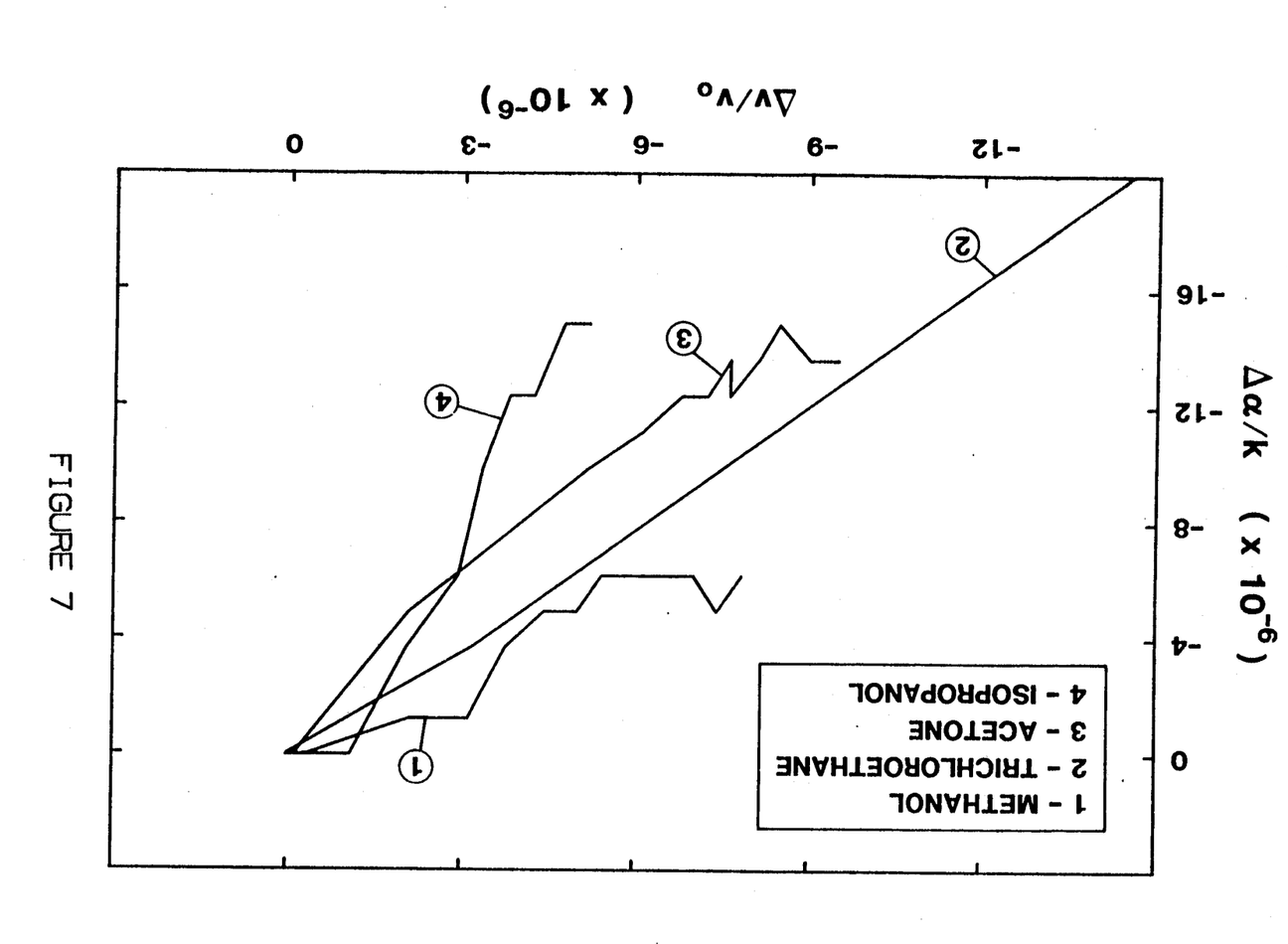
FIG. 7 is a plot of attenuation shift vs. frequency shift for a polysiloxane-coated APM device during sorption of various species.
Figure 8:
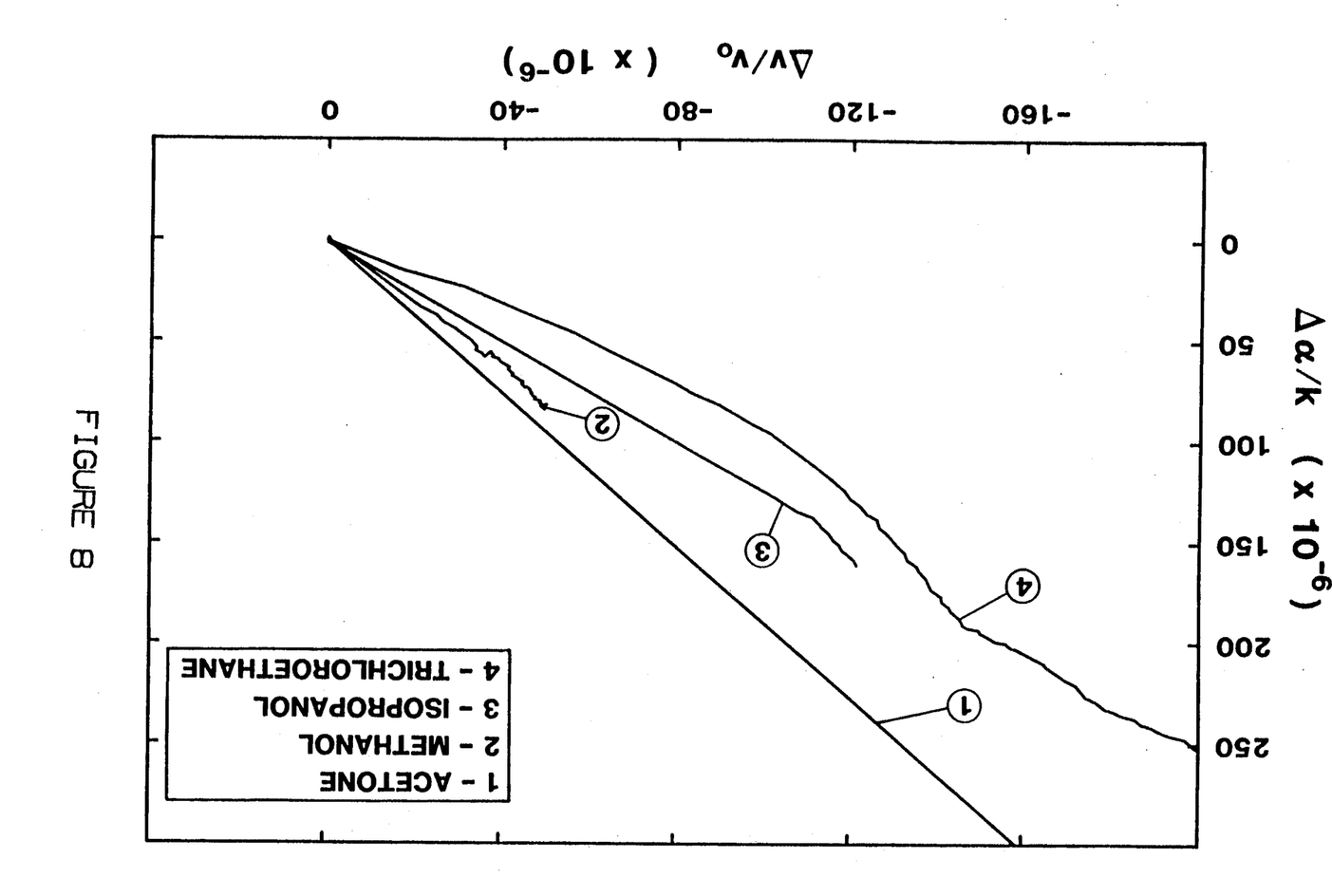
FIG. 8 is a plot of attenuation shift vs. frequency shift for a polysiloxane-coated SAW device during sorption from aqueous solutions.

The molecular identification of species sorbing from a liquid or aqueous environment is achieved with an APM device, which is more effective in liquids than SAW devices which are highly attenuated by liquids contacting the device surface. FIG. 7 illustrates results obtained using an APM device coated with a polysiloxane film and represents a response of the film to a change from a water environment to an aqueous solution containing the sorbing species, i.e., 10% by volume for methanol, isopropanol and acetone and a saturated solution of 1,1,1-trichloroethane (0.13% by weight).

Yet another technique for detecting volatile species in solution uses a semipermeable membrane such as a teflon film to hold the liquid away from the device surface while allowing volatile species in solution to pass through and sorb into a film from the gas phase. This configuration allows the use of the more sensitive SAW device for liquid phase sensing. FIG. 7 illustrates the attenuation shift and frequency shift using a polysiloxane-coated SAW device in this configuration to achieve molecular discrimination. As described above, the chemical species penetrated through a teflon barrier which held the liquid away from the device surface before sorbing into the polymer from the gas phase. The data of FIG. 7 represents a transition of the environment of the device from water to an aqueous solution containing the sorbing species at a concentration of 10% by volume for methanol, isopropanol and acetone, 10% of saturation for 1,1,1-trichloroethane, i.e., 0.013% by weight.

In many applications as environmental or process monitors, arrays of sensors using this dual output technique may be used to simultaneously provide information about multiple species. The two independent responses obtainable from each sensor allows the number of sensors to be cut in half as compared with sensors providing a single sensor response. By incorporating an RF switching unit, only a single set of electronics would be required for an array of AW sensors, making it possible to reduce the cost of a sensor array system.

We have thus invented a technique for molecular identification of chemical species with the dual output technique involving changes in polymer viscoelastic properties to provide independent responses of wave velocity and attenuation of chemical species in both gas and liquid phases. Different coatings, moreover, have different discriminating properties which have advantages for various chemical sensing systems.

A single dual-output AW sensor has the capability of providing both concentration and molecular identification for individual species, thus, these devices have practical application in situations where only one species of interest is present at a given time, for example, as in a detector for gas or liquid chromatographs. Another important application of the single sensor is in environmental monitoring situations to evaluate the chemical nature of the environment and to detect leakages or quantify and identify compounds which are often toxic in a leak or spillage situation. These environmental sensors are becoming more important because of increased regulations and awareness of environmental, safety and health issues regarding industrial processes and natural resource desecration. Such passive environmental safety monitors can discriminate between sensor signals responding to toxic chemical species and those signals in response to the presence of non-toxic chemical species, thereby providing improved protection of personnel or the environment.

Chemical process monitors using the dual output acoustic wave technique provide chemical information for improved process control. As previously mentioned, an important application of the dual output acoustic wave device is a less expensive, smaller and portable replacement to mass spectrometers for molecular identification of chromatographic peaks. Examining the dual output of this technique is used to determine molecular weight, mimicking a mass spectrometer on a chip.

We claim:

1. A method for the identification and quantification of sorbed chemical species onto a coating of a device capable of generating and receiving an acoustic wave, comprising:
   (a) measuring the changes in the velocity of the acoustic wave resulting from the sorption of the chemical species into the coating as the wave travels through the coating;
   (b) measuring the changes in the attenuation of an acoustic wave resulting from the sorption of the chemical species into the coating as the wave travels through the coating;
   (c) correlating the magnitudes of the changes of velocity with respect to changes of the attenuation of the acoustic wave to identify the sorbed chemical species.

2. The method of claim 1, further comprising:
   (d) correlating the absolute magnitude of the velocity changes to the concentration of the identified chemical species.

3. The method of claim 1, further comprising:
   (d) correlating the absolute magnitude of the attenuation changes to the concentration of the identified chemical species.

4. The method of claim 2 or 3, wherein the chemical species is in a gas phase.

5. The method of claim 2 or 3, wherein the chemical species is in a liquid phase.

6. The method of claim 2 or 3, wherein the chemical species is derived from a solid phase.

7. An apparatus for detecting and identifying at least one unknown chemical species, comprising:
   (a) an acoustic wave device capable of generating, transmitting and receiving an acoustic wave, said device coated with a material, said material having properties which change upon sorption of a chemical species;
   (b) means for measuring the velocity of an acoustic wave travelling through said material;
   (c) means for simultaneously measuring the attenuation of the acoustic wave traveling through said coating material;
   (d) sampling means to contact said acoustic wave device to said unknown chemical species for sorption of said unknown chemical species into said coating material;
   (e) means for determining the changes in both the attenuation and velocity values of said acoustic wave upon sorption of said unknown chemical species into said coating material; and
   (f) means for correlating the magnitudes of the changes of velocity with respect to the changes of the attenuations of the acoustic wave; and
   (g) means for comparing the values of the velocity and attenuation changes to known values of velocity and attenuation of known chemical species in order to identify said unknown sorbed chemical species.

8. The apparatus of claim 7, further comprising:
   (g) means for comparing the magnitude of the changes in the velocity response to known values of known chemical species in order to determine the concentration of said unknown sorbed chemical species.

9. The apparatus of claim 7, further comprising:
   (g) means for comparing the magnitude of the changes in the attenuation response to known values of known chemical species in order to determine the concentration of said unknown sorbed chemical species.

10. The apparatus of claims 8 or 9, wherein said acoustic wave device comprises a piezoelectric substrate having two interdigitated transducers at opposing ends of said substrate, one of said transducers to generate an acoustic wave, and the other of said transducers to receive an acoustic wave as said wave is transmitted through said piezoelectric substrate and generate a signal having a frequency of said acoustic wave in response thereto.

11. The apparatus of claims 8 or 9, wherein said acoustic wave device comprises a substrate having two interdigitated transducers at opposing ends of said substrate and a piezoelectric coating material on one face of each transducer, one of said transducers to generate an acoustic wave, and the other of said transducers to receive an acoustic wave as said wave is transmitted through said substrate and generate a signal having a frequency of said acoustic wave in response thereto.

12. The apparatus of claim 11, wherein said piezoelectric coating material is aluminum nitride.

13. The apparatus of claim 10 wherein said interdigitated transducers are lithographically patterned from a metallized aluminum layer cast onto the substrate.

14. The apparatus of claim 11 wherein said interdigitated transducers are lithographically patterned from a metallized layer cast onto the substrate.

15. The apparatus of claim 14 wherein said metallized layer is aluminum.

16. The apparatus of claim 14 wherein said metallized layer is gold-on-chrome composite.

17. The apparatus of claims 8 or 9, wherein said acoustic wave is a surface acoustic wave.

18. The apparatus of claims 8 or 9, wherein said acoustic wave is an acoustic plate mode.

19. The apparatus of claims 8 or 9, wherein said acoustic wave is a Lamb wave.

20. The apparatus of claims 8 or 9, wherein said acoustic wave is a Love wave.

21. The apparatus of claim 7 wherein one of said properties of said material which change upon sorption of a chemical species is mass of said material.

22. The apparatus of claim 7 wherein one of said properties of said material which change upon sorption of a chemical species is the viscoelasticity of said material.

23. The apparatus of claim 10, wherein said means for measuring the velocity of an acoustic wave traveling through said material further comprises an oscillator loop comprising:
 (a) a first coupler electrically connected to said acoustic wave device to direct a fraction of said signal's power into a first and second path;
 (b) a RF amplifier electrically connected along said first path to said first coupler to amplify said signal;
 (c) a directional coupler electrically connected to said first path to direct a portion of said signal along said first path and along a third path;
 (d) a frequency counter electrically connected along said third path to said directional coupler, said frequency counter to measure a frequency shift ($\Delta f$) of said signal which is related to the velocity shift ($\Delta v$) of said wave as it travels through said material by $\Delta f/f_o = K\Delta v/v_o$ where K is the fraction of the acoustic wave path covered by said material sorbing said unknown chemical species and $v_o$ and $f_o$ are the unperturbed velocity and frequency, respectively;
 (e) a second coupler electrically connected along said first path to said directional coupler to direct a portion of said signal along said first path into said acoustic wave device and along a fourth path;
 (f) means for measuring power of said wave electrically connected between said first and second couplers along said second and fourth paths respectively.

24. The apparatus of claim 23, wherein said means for measuring power is a vector voltmeter.

25. The apparatus of claim 23, further comprising:
 (g) two impedance matching networks, one of said networks electrically connected to said input transducer and the other of said networks electrically connected to said output transducer;
 (h) a variable attenuator electrically connected along said first path between said directional coupler and said second coupler, to reduce the power of the signal;
 (i) a phase shifter electrically connected along said first path between said RF amplifier and said directional coupler; and
 (j) a bandpass filter electrically connected along said first path between said phase shifter and said RF amplifier, to filter the signal.

26. The apparatus of claim 10, further comprising:
 (a) means for generating an input signal into said input transducer to launch an acoustic wave external, but electrically connected along a first path, to said acoustic wave device;
 (b) a first coupler electrically connected to said signal generating means along said first path between said generating means and said input transducer, said first coupler to direct a portion of said signal along a second path means for measuring the phase of said signal;
 (c) a second coupler electrically connected to said output transducer to receive an output signal, said second coupler to direct a portion of said output signal along a third path;
 (d) means for measuring the phase shift and the attenation shift of said signal electrically interconnected between said first and second couplers along said second and third paths, respectively.

27. The apparatus of claim 10, further comprising:
 (a) means for generating an input signal into said input transducer to launch an acoustic wave external, but electrically connected along a first path, to said acoustic wave device, and the frequency of said input signal from said signal generating means is maintained at a constant phase value;
 (b) a first coupler electrically connected to said signal generating means along said first path between said generating means and said input transducer, said first coupler to direct a portion of said signal along a second path means for measuring the power of said signal;
 (c) a second coupler electrically connected to said output transducer to receive an output signal, said second coupler to direct a portion of said output signal along a third path;
 (d) means for monitoring the frequency shift of said output signal, where the velocity shift ($\Delta v$) of said acoustic wave is determined from the frequency shift ($\Delta f$) using $\Delta f/f_o = K\Delta v/v_o$ where K is a fraction of said acoustic wave path covered by said coating material sorbing said unknown chemical species and $v_o$ and $f_o$ are the unperturbed velocity and frequency of said wave and signal, respectively.

28. The apparatus of claim 23, wherein said means for measuring the attenuation of said acoustic wave traveling through said material is measured using said first and second couplers to divide a portion of said signal at the input and output transducers, respectively, and to measure power level of said signal by means for measuring power.

29. The apparatus of claim 28, wherein said means for measuring power is a vector voltmeter.

30. The apparatus of claim 28, wherein said means for measuring power is a power meter.

31. The apparatus of claim 26, wherein said means for measuring the attenuation of said acoustic wave traveling through said material is measured using said first and second couplers to divide a portion of said signal at the input and output transducers, respectively, and to measure power level of said signal by means for measuring power.

32. The apparatus of claim 31, wherein said means for measuring power is a vector voltmeter.

33. The apparatus of claim 27, wherein said means for measuring the attenuation of said acoustic wave traveling through said material is measured using said first and second couplers to divide a portion of said signal at the input and output transducers, respectively, and to measure power level of said signal by means for measuring power.

34. The apparatus of claim 33, wherein said means for measuring power is a vector voltmeter.

35. The apparatus of claim 11, wherein said means for measuring the velocity of an acoustic wave traveling through said material further comprises an oscillator loop comprising:
(a) a first coupler electrically connected to said acoustic wave device to direct a fraction of said signal's power into a first and second path;
(b) a RF amplifier electrically connected along said first path to said first coupler to amplify said signal;
(c) a directional coupler electrically connected to said first path to direct a portion of said signal along said first path and along a third path;
(d) a frequency counter electrically connected along said third path to said directional coupler, said frequency counter to measure a frequency shift ($\Delta f$) of said signal which is related to the velocity shift ($\Delta v$) of said wave as it travels through said material by $\Delta f/f_o = K\Delta v/v_o$ where K is the fraction of the acoustic wave path covered by said material sorbing said unknown chemical species and $v_o$ and $f_o$ are the unperturbed velocity and frequency, respectively;
(e) a second coupler electrically connected along said first path to said directional coupler to direct a portion of said signal along said first path into said acoustic wave device and along a fourth path;
(f) means for measuring power of said wave electrically connected between said first and second couplers along said second and fourth paths respectively.

36. The apparatus of claim 35, wherein said means for measuring power is a vector voltmeter.

37. The apparatus of claim 35, further comprising:
(g) two impedance matching networks, one of said networks electrically connected to said input transducer and the other of said networks electrically connected to said output transducer;
(h) a variable attenuator electrically connected along said first path between said directional coupler and said second coupler, to reduce the power of the signal;
(i) a phase shifter electrically connected along said first path between said RF amplifier and said directional coupler; and
(j) a bandpass filter electrically connected along said first path between said phase shifter and said RF amplifier, to filter the signal.

38. The apparatus of claim 11, further comprising:
(a) means for generating an input signal into said input transducer to launch an acoustic wave external, but electrically connected along a first path, to said acoustic wave device;
(b) a first coupler electrically connected to said signal generating means along said first path between said generating means and said acoustic wave device, said first coupler to direct a portion of said signal along a second path means for measuring the phase shift of said signal;
(c) a second coupler electrically connected to said acoustic wave device along said first path to receive an output signal from said acoustic wave device, said second coupler to direct a portion of said output signal along a third path for measuring the phase shift and the velocity shift of said output signal; and
(d) means for measuring phase and monitoring the frequency shift of said signal electrically interconnected between said first and second couplers along said second and third paths, respectively.

39. The apparatus of claim 11, further comprising:
(a) means for generating an input signal into said input transducer to launch an acoustic wave external, but electrically connected along a first path, to said acoustic wave device, and the frequency of said input signal from said signal generating means is maintained at a constant phase value;
(b) a first coupler electrically connected to said signal generating means along said first path between said generating means and said input transducer, said first coupler to direct a portion of said signal along a second path means for measuring the power of said signal;
(c) a second coupler electrically connected to said output transducer to receive an output signal, said second coupler to direct a portion of said output signal along a third path;
(d) means for monitoring frequency shift where the velocity shift ($\Delta v$) of said acoustic wave is determined from the frequency shift ($\Delta f$) using $\Delta f/f_o = K\Delta v/v_o$ where K is a fraction of said acoustic wave path covered by said coating material sorbing said unknown chemical species and $v_o$ and $f_o$ are the unperturbed velocity and frequency of said wave and signal, respectively.

40. The apparatus of claim 35, wherein said means for measuring the attenuation of said acoustic wave traveling through said material is measured using said first and second couplers to divide a portion of said signal at the input and output transducers, respectively, and to measure power level of said signal by means for measuring power.

41. The apparatus of claim 40, wherein said means for measuring power is a vector voltmeter.

42. The apparatus of claim 38, wherein said means for measuring the attenuation of said acoustic wave traveling through said material is measured using said first and second couplers to divide a portion of said signal at the input and output transducers, respectively, and to measure power level of said signal by a vector voltmeter.

43. The apparatus of claim 39, wherein said means for measuring the attenuation of said acoustic wave traveling through said material is measured using said first and second couplers to divide a portion of said signal at the input and output transducers, respectively, and to measure power level of said signal by a vector voltmeter.

44. The apparatus of claim 7, wherein said sampling means further comprises a semipermeable membrane surrounding said acoustic wave device which permits said unknown chemical species in a liquid solution to be transported across said membrane into a gas phase to be contacted with said acoustic wave device.

45. An array comprising a plurality of the apparatus of claim 7, each apparatus electrically interconnected for the purpose of detecting multiple chemical species.

46. The array of claim 45, further comprising a pattern recognition means interconnected to said array, said pattern recognitions means to identify and quantify said multiple chemical species based on a plurality of correlated velocity and attenuation changes, each of said correlated velocity and attenuation changes associated with one of said sensors, said plurality of correlated changes analyzed by said pattern recognition menus.

47. An apparatus for detecting and identifying at least one unknown chemical species, comprising:
(a) at least one acoustic wave device, wherein said acoustic wave device comprises a piezoelectric substrate having two interdigitated transducers at opposing ends of said substrate, one of said transducers to generate an acoustic wave, and the other of said transducers to receive an acoustic wave as said wave is transmitted through said piezoelectric substrate and to generate a signal having a frequency of said acoustic wave in response thereto, said substrate coated with a material, said material having properties which change upon sorption of a chemical species;
(b) an oscillator loop to measure the velocity of an acoustic wave traveling through said material, said loop further comprising a first coupler electrically connected to said acoustic wave device to direct a fraction of said signal's power into a first and second path, a RF amplifier electrically connected along said first path to said first coupler to amplify said signal, a directional coupler electrically connected to said first path to direct a portion of said signal along said first path and along a third path, a frequency counter electrically connected along said third path to said directional coupler, said frequency counter to measure a frequency shift ($\Delta f$) of said signal which is related to the velocity shift ($\Delta v$) of said wave as it travels through said material by $\Delta f/f_o = K\Delta v/v_o$ where K is the fraction of the acoustic wave path covered by said material sorbing said unknown chemical species and $v_o$ and $f_o$ are the unperturbed velocity and frequency, respectively, a second coupler electrically connected along said first path to said directional coupler to direct a portion of said signal along said first path into said acoustic wave device and along a fourth path, and a bandpass filter electrically connected along said first path between said directional coupler and said RF amplifier, to filter the signal
(c) a vector voltmeter electrically connected between said first and second couplers along said second and fourth paths to divide said signal at said output transducer and to divide said signal at said input transducer, respectively, for measuring the power level of said signal which power level is proportional to the attenuation of power of said wave traveling through said material;
(d) sampling means to contact said acoustic wave device to said unknown chemical species for sorption of said unknown chemical species into said coating material;
(e) microprocessing means for acquiring data indicating changes in and storing the values of said changes of both the attenuation and velocity values of said acoustic wave upon sorption of said unknown chemical species;
(f) a microprocessing analysis means for comparing the values of the velocity and attenuation changes to known values of known chemical species in order to identify said unknown sorbed chemical species; and
(g) microprocessing comparing means for comparing the absolute value of the changes in the velocity response to known values of known chemical species in order to determine the concentration of said unknown sorbed chemical species.

48. A method for the identification and quantification of sorbed chemical species into a coating of a device capable of generating, transmitting and receiving an acoustic wave, comprising:
(a) measuring the changes in the velocity of the acoustic wave resulting from the sorption of the chemical species into the coating as the wave travels through the coating;
(b) measuring the changes in the attenuation of an acoustic wave resulting from the sorption of the chemical species into the coating as the wave travels through the coating;
(c) correlating the magnitudes of the changes of velocity with respect to changes of the attenuation of the acoustic wave to identify the sorbed chemical species.
(d) correlating the absolute magnitude of the velocity changes to the concentration of the identified chemical species.

* * * * *